US007728122B2

(12) United States Patent
Dasgupta et al.

(10) Patent No.: US 7,728,122 B2
(45) Date of Patent: Jun. 1, 2010

(54) RTBV PLANT PROMOTER AND PROCESS THEREOF

(75) Inventors: Indranil Dasgupta, New Delhi (IN); Saloni Mathur, New Delhi (IN)

(73) Assignees: University of Delhi, New Delhi (IN); Department of Biotechnology, New Delhi (IN)

( * ) Notice: Subject to any disclaimer, the term of this patent is extended or adjusted under 35 U.S.C. 154(b) by 279 days.

(21) Appl. No.: 11/661,452

(22) PCT Filed: Aug. 19, 2005

(86) PCT No.: PCT/IN2005/000285

§ 371 (c)(1),
(2), (4) Date: Sep. 24, 2007

(87) PCT Pub. No.: WO2007/010545

PCT Pub. Date: Jan. 25, 2007

(65) Prior Publication Data

US 2008/0282431 A1   Nov. 13, 2008

(30) Foreign Application Priority Data

Aug. 30, 2004   (IN)   .................. 1422/DEL/2004

(51) Int. Cl.
*C07H 21/04* (2006.01)
*C12N 15/82* (2006.01)
(52) U.S. Cl. .................. 536/24.1; 800/287; 800/278
(58) Field of Classification Search .................. None
See application file for complete search history.

(56) References Cited

U.S. PATENT DOCUMENTS

| 5,824,857 | A   | 10/1998 | Beachy et al. |
| 6,528,701 | B1  | 3/2003  | Wang et al. |
| 6,664,387 | B2  | 12/2003 | Chung et al. |
| 6,693,227 | B1  | 2/2004  | Gittins et al. |
| 6,713,665 | B2  | 3/2004  | Crane, III et al. |
| 7,276,370 | B2 * | 10/2007 | Beachy et al. ............ 435/320.1 |

FOREIGN PATENT DOCUMENTS

WO   02/46366 A2   6/2002

OTHER PUBLICATIONS

Cornejo et al.; "Activity of a Maize Ubiquitin Promoter in Transgenic Rice"; Plant Molecular Biology; 1993; pp. 567-581; vol. 23.
Jang et al.; "High-Level and Ubiquitous Expression of the Rice Cytochrome c Gene *OsCc*1 and its Promoter Activity in Transgenic Plants Provides a Useful Promoter for Transgenesis of Monocots"; Plant Physiology; Aug. 2002; pp. 1473-1481; vol. 129.
Kloti et al.; "Upstream and downstream Sequence Elements Determine the Specificity of the Rice Tungro Bacilliform Virus Promoter and Influence RNA Production After Transcription Initiation"; Plant Molecular Biology; 1999; pp. 249-266; vol. 40.
Nath et al.; "Molecular Analysis of Two Complete Rice Tungro Bacilliform Virus Genomic Sequences from India"; Arch Virol; 2002; pp. 1173-1187; vol. 147.
Toki et al.; "Expression of a Maise Ubiquitin Gene Promoter-bar Chimeric Gene in Transgenic Rice Plant"; Plant Physiol.; 1992; pp. 1503-1507; vol. 100.
Wilmink et al.; "Activity of Constitutive Promoters in Various Species from the Lillaceae"; Plant Molecular Biology; 1995; pp. 949-955; vol. 28.
Ye et al.; "Engineering the Provitamin A (β-Carotene) Biosynthetic Pathway into (Carotenoid-Free) Rice Endosperm"; Science; Jan. 14, 2000; pp. 303-305; vol. 287.
Yin et al.; "The Regulatory Regions of the Rice Tungro Bacilliform Virus Promoter and Interacting Nuclear Factors in Rice (*Oryza sativa* L.)"; The Plant Journal; 1995; pp. 969-980; vol. 7; No. 6.
Yin et al.; "Promoter Elements required for Phloem-Specific Gene Expression from the RTBV Promoter in Rice"; The Plant Journal; 1997; pp. 1179-1188; vol. 12; No. 5.

* cited by examiner

*Primary Examiner*—David H Kruse
*Assistant Examiner*—Li Zheng
(74) *Attorney, Agent, or Firm*—The Webb Law Firm

(57) ABSTRACT

The present invention relates to isolation and characterization of novel nucleotide sequences from rice tungro bacilliform virus (RTBV) showing promoter activity in plants. The present invention further relates to the analysis of the functional domains of RTBV promoters by fusing full-length and deleted versions of the RTBV promoter sequences with the bacterial reporter gene GUS. The invention also relates to the study of the expression of the reporter gene in various tissues of transgenic rice and tobacco plants during different stages of development. The present invention also describes an RTBV promoter and its deletions which function in a constitutive or tissue-specific manner to drive the expression of the heterologous nucleic acid sequences in both monocot and dicot plants, cells and tissues.

22 Claims, 3 Drawing Sheets

FP1▶                                                    FP2▶
tgtcctgcaccacctcaatggaagaagaatatgcccacaggctggaggcataaagagatgatccaaagataaaggaacaa FP3 ▶                          FP4 ▶                            FP5▶
agcagcaaagcatcaataaaagaagactgaagacataaaggggggaatccactttaaattattgtacctctacaattattg FP6 ▶   FP7 ▶
taagagtgtgtaaaatctagcctacccctgaacactcctatataaggagaagtagtctgcatgtaataggcattcgaaat ◀RP9                              ◀RP8
ccacacacccagagtagcacacacttccacaagagcaagagaagagctgatcttctcacctcctcttcaaagaaggatta ◀RP7
gctgcaatggctcaggtcagtgagtagtcgtctttaaggttcctctaggaacctctgtgtcatatgtattgtatcatgtt ◀RP6
tgtatcatcaagaacttatccgctgcatgaataaagctctatattgttgtttacactccttagataagatatgaagccat acccgtttcttaaatcaatagttctaagataattctagcatgaaaaaggggggctaaaggggggaagaagtaccgtcagggc ◀RP5
gtgtgatgccaagggaacaagtaccatgaataccctaataagtgctagagggaagataagaactaacgaaataaggaaca ◀RP4
tttggtagctggtttcttattatcattatcaagtagctcttcctcatcacgaaaactgcaaaggcctgccaaccctaggc ◀RP3
tgaaacagtgactaggccgaggaattgcgaaaagatagggggggtgcctacatctggtatcagagcgatgttcgaactt ◀RP2      ◀RP1
aagggaaattttgatacaaacttatacatacatttacatatgttctgaagagggatcttactttctcaaatattga Figure 1
The full sequence of the 876 bp RTBV promoter. The primers have been indicated on top of the 5'base (forward primer, FP) or 3'base (reverse primer, RP) of the primer, and have been coloured red. The forward and reverse nature of the primer is indicated by the arrow heads.

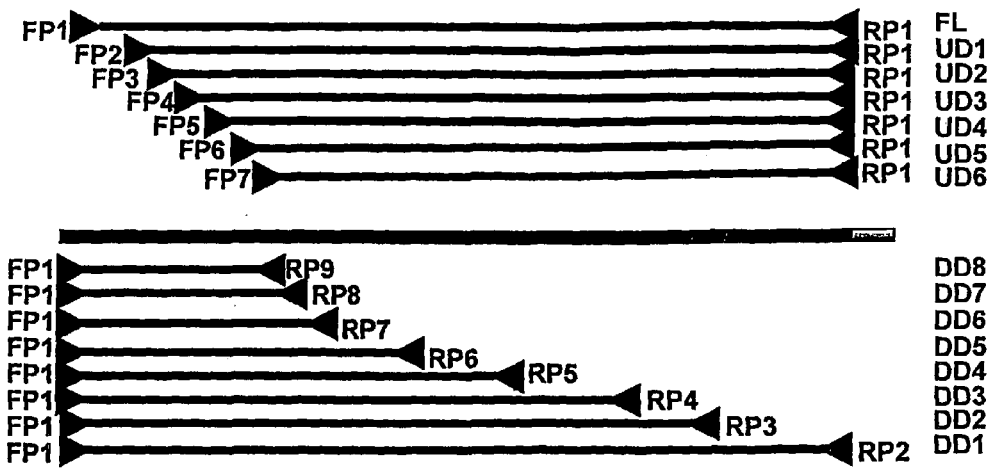

Figure 2
Schematic representation of PCR-generated RTBV promoter deletion fragments. The primers are designated as FP1-7 for forward primers and as RP1-9 for reverse primers. The, rectangular box depicts a section of RTBV genome, 900bp in size, the arrowheads denote approximate primer position and the horizontal line joining them the expected fragments. The respective promoter deletion constructs have been written to the right of the fragments, where the upstream deletion are named as UD1-6 and downstream deletion as DD1-8

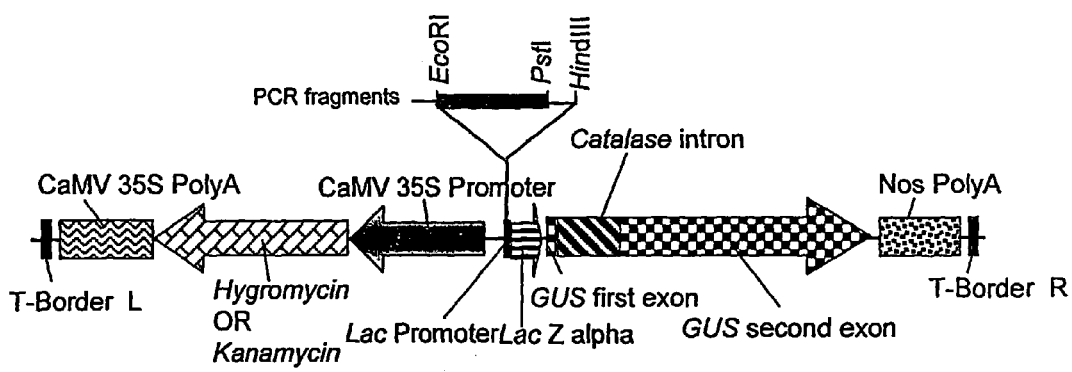

Figure 3
Schematic representation of the T-DNA region of the promoterless vector, pCAMBIA1381z used for cloning in rice or tobacco having the selectable marker genes hygromycin or kanamycin, respectively

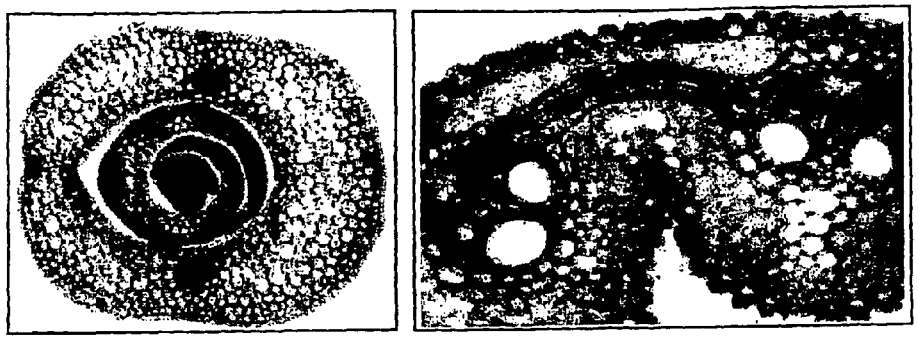
FL, UD1,
UD2, UD3,
UD4, UD5,
DD3, DD4
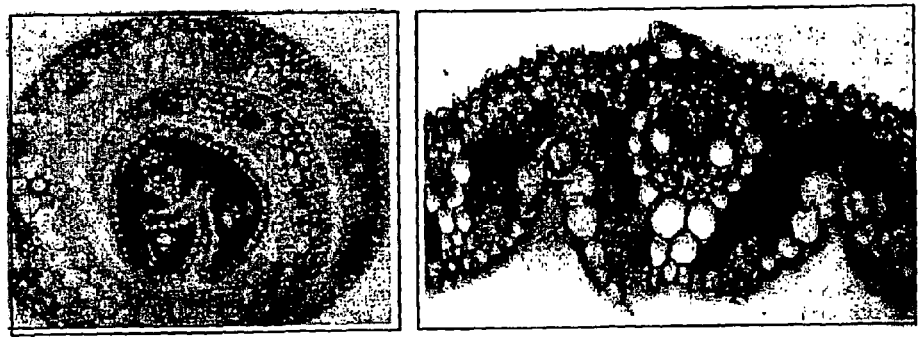
DD7,
DD8
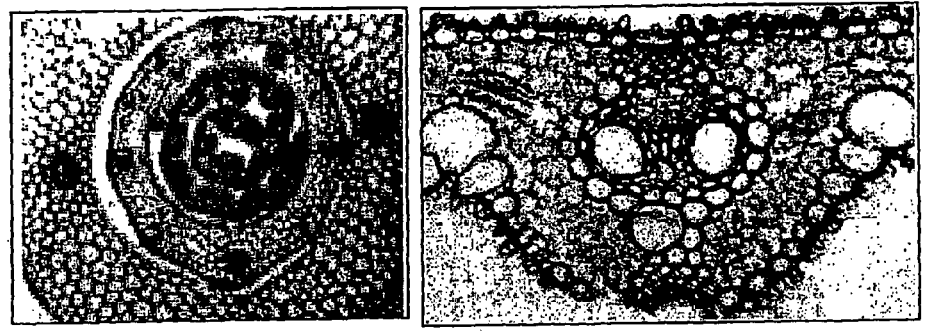
DD5,
DD6
YOUNG SHOOT         MATURE LEAF
Figure 4
Hand-cut sections of transgenic rice. The blue colour shows promoter activity in the respective tissues. The constructs exhibiting the pattern are denoted as FL, UD1-5, DD3-8 on the right

SEQUENCE LISTING

```
<160> NUMBER OF SEQ ID NOS: 31

<210> SEQ ID NO 1
<211> LENGTH: 876
<212> TYPE: DNA
<213> ORGANISM: Rice Tungro Bacilliform Virus

<400> SEQUENCE: 1
tgtcctgcac cacctcaatg gaagaagaat atgcccacag gctggaggca taaagagatg      60
atccaaagat aaaggaacaa agcagcaaag catcaataaa agaagactga agacataaag     120
ggggaatcca ctttaaatta ttgtacctct acaattattg taagagtgtg taaaatctag     180 cctaccoctg aacactccta tataaggaga agtagtctgc atgtaatagg cattcgaaat     240
ccacacaccc agagtagcac acacttccac aagagcaaga gaagagctga tcttctcacc     300
```

```
tcctcttcaa agaaggatta gctgcaatgg ctcaggtcag tgagtagtcg tctttaaggt    360
tcctctagga acctctgtgt catatgtatt gtatcatgtt tgtatcatca agaacttatc    420
cgctgcatga ataaagctct atattgttgt ttacactcct tagataagat atgaagccat    480
acccgtttct taaatcaata gttctaagat aattctagca tgaaaaaggg ggctaaaggg    540
ggaagaagta ccgtcagggc gtgtgatgcc aagggaacaa gtaccatgaa tacccctaata   600 agtgctagag ggaagataag aactaacgaa ataaggaaca tttggtagct ggtttcttat    660
tatcattatc aagtagctct tcctcatcac gaaaactgca aaggcctgcc aaccctaggc    720
tgaaacagtg actaggccga ggaattgcga aagataggg ggggtgccta catctggtat    780
cagagcgatg ttcgaacttt aagggaaatt ttgatacaaa cttatacata catttacata    840
tgttctgaag agggatctta ctttctcaaa tattga                              876

<210> SEQ ID NO 2
<211> LENGTH: 818
<212> TYPE: DNA
<213> ORGANISM: Rice Tungro Bacilliform Virus

<400> SEQUENCE: 2
tgatccaaag ataaaggaac aaagcagcaa agcatcaata aaagaagact gaagacataa    60
agggggaatc cactttaaat tattgtacct ctacaattat tgtaagagtg tgtaaaatct    120
agcctacccc tgaacactcc tatataagga gaagtagtct gcatgtaata ggcattcgaa    180
atccacacac ccagagtagc acacacttcc acaagagcaa gagaagagct gatcttctca    240
cctcctcttc aaagaaggat tagctgcaat ggctcaggtc agtgagtagt cgtctttaag    300
gttcctctag gaacctctgt gtcatatgta ttgtatcatg tttgtatcat caagaactta    360
tccgctgcat gaataaagct ctatattgtt gtttacactc cttagataag atatgaagcc    420
atacccgttt cttaaatcaa tagttctaag ataattctag catgaaaaag ggggctaaag    480
ggggaagaag taccgtcagg gcgtgtgatg ccaagggaac aagtaccatg aatacccctaa   540 taagtgctag agggaagata agaactaacg aaataaggaa catttggtag ctggtttctt    600
attatcatta tcaagtagct cttcctcatc acgaaaactg caaaggcctg ccaaccctag    660
gctgaaacag tgactaggcc gaggaattgc gaaagatagg gggggtgcc tacatctggt    720 atcagagcga tgttcgaact ttaagggaaa ttttgataca aacttataca tacatttaca    780
tatgttctga gagggatct actttctca atattga                              818

<210> SEQ ID NO 3
<211> LENGTH: 789
<212> TYPE: DNA
<213> ORGANISM: Rice Tungro Bacilliform Virus

<400> SEQUENCE: 3
aagcatcaat aaaagaagac tgaagacata aagggggaat ccactttaaa ttattgtacc    60
tctacaatta ttgtaagagt gtgtaaaatc tagcctaccc ctgaacactc ctatataagg    120
agaagtagtc tgcatgtaat aggcattcga atccacacac ccagagtagc acacacttc    180 cacaagagca agagaagagc tgatcttctc acctcctctt caaagaagga ttagctgcaa    240
tggctcaggt cagtgagtag tcgtctttaa ggttcctcta ggaacctctg tgtcatatgt    300
attgtatcat gtttgtatca tcaagaactt atccgctgca tgaataaagc tctatattgt    360
tgtttacact ccttagataa gatatgaagc catacccgtt tcttaaatca atagttctaa    420
gataattcta gcatgaaaaa gggggctaaa ggggaagaa gtaccgtcag ggcgtgtgat    480
```

```
gccaagggaa caagtaccat gaatacccta ataagtgcta gagggaagat aagaactaac    540
gaaataagga acatttggta gctggtttct tattatcatt atcaagtagc tcttcctcat    600
cacgaaaact gcaaaggcct gccaacccta ggctgaaaca gtgactaggc cgaggaattg    660
cgaaaagata gggggggtgc ctacatctgg tatcagagcg atgttcgaac tttaagggaa    720
attttgatac aaacttatac atacatttac atatgttctg aagagggatc ttactttctc    780
aaatattga                                                            789
```

<210> SEQ ID NO 4
<211> LENGTH: 754
<212> TYPE: DNA
<213> ORGANISM: Rice Tungro Bacilliform Virus

<400> SEQUENCE: 4

```
ggaatccact ttaaattatt gtacctctac aattattgta agagtgtgta aaatctagcc     60 taccctgaa cactcctata aaggagaag tagtctgcat gtaataggca ttcgaaatcc     120
acacacccag agtagcacac acttccacaa gagcaagaga gagctgatc ttctcacctc    180 ctcttcaaag aaggattagc tgcaatggct caggtcagtg agtagtcgtc tttaaggttc    240
ctctaggaac ctctgtgtca tatgtattgt atcatgtttg tatcatcaag aacttatccg    300
ctgcatgaat aaagctctat attgttgttt acactcctta gataagatat gaagccatac    360
ccgtttctta aatcaatagt tctaagataa ttctagcatg aaaaagggg ctaaagggg     420 aagaagtacc gtcagggcgt gtgatgccaa gggaacaagt accatgaata ccctaataag    480
tgctagaggg aagataagaa ctaacgaaat aaggaacatt tggtagctgg tttcttatta    540
tcattatcaa gtagctcttc ctcatcacga aaactgcaaa ggcctgccaa ccctaggctg    600
aaacagtgac taggccgagg aattgcgaaa agatagggg ggtgcctaca tctggtatca    660
gagcgatgtt cgaactttaa gggaaatttt gatacaaact tatacataca tttacatatg    720
ttctgaagag ggatcttact ttctcaaata ttga                                754
```

<210> SEQ ID NO 5
<211> LENGTH: 718
<212> TYPE: DNA
<213> ORGANISM: Rice Tungro Bacilliform Virus

<400> SEQUENCE: 5

```
tgtaagagtg tgtaaaatct agcctacccc tgaacactcc tatataagga gaagtagtct     60
gcatgtaata ggcattcgaa atccacacac ccagagtagc acacacttcc acaagagcaa    120
gagaagagct gatcttctca cctcctcttc aaagaaggat tagctgcaat ggctcaggtc    180
agtgagtagt cgtctttaag gttcctctag gaacctctgt gtcatatgta ttgtatcatg    240
tttgtatcat caagaactta tccgctgcat gaataaagct ctatattgtt gtttacactc    300
cttagataag atatgaagcc ataccgtttt cttaaatcaa tagttctaag ataattctag    360
catgaaaaag ggggctaaag ggggaagaag taccgtcagg gcgtgtgatg ccaagggaac    420
aagtaccatg aatacctaa taagtgctag agggaagata agaactaacg aaataaggaa    480
catttggtag ctggtttctt attatcatta tcaagtagct cttcctcatc acgaaaactg    540
caaaggcctg ccaaccctag gctgaaacag tgactaggcc gaggaattgc gaaaagatag    600
ggggggtgcc tacatctggt atcagagcga tgttcgaact ttaagggaaa ttttgataca    660
aacttataca tacatttaca tatgttctga agagggatct tactttctca aatattga     718
```

<210> SEQ ID NO 6
<211> LENGTH: 681
<212> TYPE: DNA
<213> ORGANISM: Rice Tungro Bacilliform Virus

<400> SEQUENCE: 6

```
tcctatataa ggagaagtag tctgcatgta ataggcattc gaaatccaca cacccagagt      60
agcacacact tccacaagag caagagaaga gctgatcttc tcacctcctc ttcaaagaag     120
gattagctgc aatggctcag gtcagtgagt agtcgtcttt aaggttcctc taggaacctc     180
tgtgtcatat gtattgtatc atgtttgtat catcaagaac ttatccgctg catgaataaa     240
gctctatatt gttgtttaca ctccttagat aagatatgaa gccatacccg tttcttaaat     300
caatagttct aagataattc tagcatgaaa aggggggcta aggggggaag aagtaccgtc     360
agggcgtgtg atgccaaggg aacaagtacc atgaataccc taataagtgc tagagggaag     420
ataagaacta acgaaataag gaacatttgg tagctggttt cttattatca ttatcaagta     480
gctcttcctc atcacgaaaa ctgcaaggc ctgccaaccc taggctgaaa cagtgactag      540
gccgaggaat tgcgaaaaga taggggggt gcctacatct ggtatcagag cgatgttcga      600
actttaaggg aaattttgat acaaacttat acatacattt acatatgttc tgaagaggga     660
tcttactttc tcaaatattg a                                               681
```

<210> SEQ ID NO 7
<211> LENGTH: 671
<212> TYPE: DNA
<213> ORGANISM: Rice Tungro Bacilliform Virus

<400> SEQUENCE: 7

```
ggagaagtag tctgcatgta ataggcattc gaaatccaca cacccagagt agcacacact      60
tccacaagag caagagaaga gctgatcttc tcacctcctc ttcaaagaag gattagctgc     120
aatggctcag gtcagtgagt agtcgtcttt aaggttcctc taggaacctc tgtgtcatat     180
gtattgtatc atgtttgtat catcaagaac ttatccgctg catgaataaa gctctatatt     240
gttgtttaca ctccttagat aagatatgaa gccatacccg tttcttaaat caatagttct     300
aagataattc tagcatgaaa aggggggcta aggggggaag aagtaccgtc agggcgtgtg     360
atgccaaggg aacaagtacc atgaataccc taataagtgc tagagggaag ataagaacta     420
acgaaataag gaacatttgg tagctggttt cttattatca ttatcaagta gctcttcctc     480
atcacgaaaa ctgcaaggc ctgccaaccc taggctgaaa cagtgactag gccgaggaat     540
tgcgaaaaga taggggggt gcctacatct ggtatcagag cgatgttcga actttaaggg     600
aaattttgat acaaacttat acatacattt acatatgttc tgaagaggga tcttactttc    660
tcaaatattg a                                                          671
```

<210> SEQ ID NO 8
<211> LENGTH: 862
<212> TYPE: DNA
<213> ORGANISM: Deleted Verison DD1 of Rice Tungro Bacilliform Virus

<400> SEQUENCE: 8

```
tgtcctgcac cacctcaatg gaagaagaat atgcccacag gctggaggca taaagagatg      60
atccaaagat aaaggaacaa agcagcaaag catcaataaa agaagactga agacataaag     120
ggggaatcca cttaaatta ttgtacctct acaattattg taagagtgtg taaaatctag      180
cctacccctg aacactccta tataaggaga agtagtctgc atgtaatagg cattcgaaat     240
```

-continued

```
ccacacaccc agagtagcac acacttccac aagagcaaga gaagagctga tcttctcacc    300
tcctcttcaa agaaggatta gctgcaatgg ctcaggtcag tgagtagtcg tctttaaggt    360
tcctctagga acctctgtgt catatgtatt gtatcatgtt tgtatcatca agaacttatc    420
cgctgcatga ataaagctct atattgttgt ttacactcct tagataagat atgaagccat    480
acccgtttct taaatcaata gttctaagat aattctagca tgaaaaaggg ggctaaaggg    540
ggaagaagta ccgtcagggc gtgtgatgcc aagggaacaa gtaccatgaa tacctaata     600 agtgctagag ggaagataag aactaacgaa ataaggaaca tttggtagct ggtttcttat    660
tatcattatc aagtagctct tcctcatcac gaaaactgca aaggcctgcc aaccctaggc    720
tgaaacagtg actaggccga ggaattgcga aaagataggg ggggtgccta catctggtat    780
cagagcgatg ttcgaacttt aagggaaatt ttgatacaaa cttatacata catttacata    840
tgttctgaag agggatctta ct                                             862
```

<210> SEQ ID NO 9
<211> LENGTH: 793
<212> TYPE: DNA
<213> ORGANISM: Rice Tungro Bacilliform Virus

<400> SEQUENCE: 9

```
tgtcctgcac cacctcaatg gaagaagaat atgcccacag gctggaggca taaagagatg     60
atccaaagat aaaggaacaa agcagcaaag catcaataaa agaagactga agacataaag    120
ggggaatcca ctttaaatta ttgtacctct acaattattg taagagtgtg taaaatctag    180 cctaccctg aacactccta tataaggaga agtagtctgc atgtaatagg cattcgaaat     240
ccacacaccc agagtagcac acacttccac aagagcaaga gaagagctga tcttctcacc    300
tcctcttcaa agaaggatta gctgcaatgg ctcaggtcag tgagtagtcg tctttaaggt    360
tcctctagga acctctgtgt catatgtatt gtatcatgtt tgtatcatca agaacttatc    420
cgctgcatga ataaagctct atattgttgt ttacactcct tagataagat atgaagccat    480
acccgtttct taaatcaata gttctaagat aattctagca tgaaaaaggg ggctaaaggg    540
ggaagaagta ccgtcagggc gtgtgatgcc aagggaacaa gtaccatgaa tacctaata     600 agtgctagag ggaagataag aactaacgaa ataaggaaca tttggtagct ggtttcttat    660
tatcattatc aagtagctct tcctcatcac gaaaactgca aaggcctgcc aaccctaggc    720
tgaaacagtg actaggccga ggaattgcga aaagataggg ggggtgccta catctggtat    780
cagagcgatg ttc                                                       793
```

<210> SEQ ID NO 10
<211> LENGTH: 691
<212> TYPE: DNA
<213> ORGANISM: Rice Tungro Bacilliform Virus

<400> SEQUENCE: 10

```
tgtcctgcac cacctcaatg gaagaagaat atgcccacag gctggaggca taaagagatg     60
atccaaagat aaaggaacaa agcagcaaag catcaataaa agaagactga agacataaag    120
ggggaatcca ctttaaatta ttgtacctct acaattattg taagagtgtg taaaatctag    180 cctaccctg aacactccta tataaggaga agtagtctgc atgtaatagg cattcgaaat     240
ccacacaccc agagtagcac acacttccac aagagcaaga gaagagctga tcttctcacc    300
tcctcttcaa agaaggatta gctgcaatgg ctcaggtcag tgagtagtcg tctttaaggt    360
```

-continued

```
tcctctagga acctctgtgt catatgtatt gtatcatgtt tgtatcatca agaacttatc    420
cgctgcatga ataaagctct atattgttgt ttacactcct tagataagat atgaagccat    480
acccgtttct taaatcaata gttctaagat aattctagca tgaaaaaggg ggctaaaggg    540
ggaagaagta ccgtcagggc gtgtgatgcc aagggaacaa gtaccatgaa tacccctaata   600 agtgctagag ggaagataag aactaacgaa ataaggaaca tttggtagct ggtttcttat    660
tatcattatc aagtagctct tcctcatcac g                                   691
```

<210> SEQ ID NO 11
<211> LENGTH: 581
<212> TYPE: DNA
<213> ORGANISM: Rice Tungro Bacilliform Virus

<400> SEQUENCE: 11

```
tgtcctgcac cacctcaatg gaagaagaat atgcccacag gctggaggca taaagagatg     60
atccaaagat aaaggaacaa agcagcaaag catcaataaa agaagactga agacataaag    120
ggggaatcca ctttaaatta ttgtacctct acaattattg taagagtgtg taaaatctag    180
cctacccctg aacactccta tataaggaga agtagtctgc atgtaatagg cattcgaaat    240
ccacacaccc agagtagcac acacttccac aagagcaaga gaagagctga tcttctcacc    300
tcctcttcaa agaaggatta gctgcaatgg ctcaggtcag tgagtagtcg tctttaaggt    360
tcctctagga acctctgtgt catatgtatt gtatcatgtt tgtatcatca agaacttatc    420
cgctgcatga ataaagctct atattgttgt ttacactcct tagataagat atgaagccat    480
acccgtttct taaatcaata gttctaagat aattctagca tgaaaaaggg ggctaaaggg    540
ggaagaagta ccgtcagggc gtgtgatgcc aagggaacaa g                       581
```

<210> SEQ ID NO 12
<211> LENGTH: 426
<212> TYPE: DNA
<213> ORGANISM: Rice Tungro Bacilliform Virus

<400> SEQUENCE: 12

```
tgtcctgcac cacctcaatg gaagaagaat atgcccacag gctggaggca taaagagatg     60
atccaaagat aaaggaacaa agcagcaaag catcaataaa agaagactga agacataaag    120
ggggaatcca ctttaaatta ttgtacctct acaattattg taagagtgtg taaaatctag    180
cctacccctg aacactccta tataaggaga agtagtctgc atgtaatagg cattcgaaat    240
ccacacaccc agagtagcac acacttccac aagagcaaga gaagagctga tcttctcacc    300
tcctcttcaa agaaggatta gctgcaatgg ctcaggtcag tgagtagtcg tctttaaggt    360
tcctctagga acctctgtgt catatgtatt gtatcatgtt tgtatcatca agaacttatc    420
cgctgc                                                              426
```

<210> SEQ ID NO 13
<211> LENGTH: 325
<212> TYPE: DNA
<213> ORGANISM: Rice Tungro Bacilliform Virus

<400> SEQUENCE: 13

```
tgtcctgcac cacctcaatg gaagaagaat atgcccacag gctggaggca taaagagatg     60
atccaaagat aaaggaacaa agcagcaaag catcaataaa agaagactga agacataaag    120
ggggaatcca ctttaaatta ttgtacctct acaattattg taagagtgtg taaaatctag    180
cctacccctg aacactccta tataaggaga agtagtctgc atgtaatagg cattcgaaat    240
```

-continued

```
ccacacaccc agagtagcac acacttccac aagagcaaga gaaagagctga tcttctcacc    300 tcctcttcaa agaaggatta gctgc                                          325

<210> SEQ ID NO 14
<211> LENGTH: 289
<212> TYPE: DNA
<213> ORGANISM: Rice Tungro Baciliform Virus

<400> SEQUENCE: 14
tgtcctgcac cacctcaatg gaagaagaat atgcccacag gctggaggca taaagagatg    60
atccaaagat aaaggaacaa agcagcaaag catcaataaa agaagactga agacataaag   120
ggggaatcca ctttaaatta ttgtacctct acaattattg taagagtgtg taaaatctag   180
cctacccctg aacactccta tataaggaga agtagtctgc atgtaatagg cattcgaaat   240
ccacacaccc agagtagcac acacttccac aagagcaaga gaaagagctg              289

<210> SEQ ID NO 15
<211> LENGTH: 254
<212> TYPE: DNA
<213> ORGANISM: Rice Tungro Baciliform Virus

<400> SEQUENCE: 15
tgtcctgcac cacctcaatg gaagaagaat atgcccacag gctggaggca taaagagatg    60
atccaaagat aaaggaacaa agcagcaaag catcaataaa agaagactga agacataaag   120
ggggaatcca ctttaaatta ttgtacctct acaattattg taagagtgtg taaaatctag   180
cctacccctg aacactccta tataaggaga agtagtctgc atgtaatagg cattcgaaat   240
ccacacaccc agag                                                     254

<210> SEQ ID NO 16
<211> LENGTH: 28
<212> TYPE: DNA
<213> ORGANISM: Rice Tungro Baciliform Virus

<400> SEQUENCE: 16
cggaattctg tcctgcacca cctcaatg                                       28

<210> SEQ ID NO 17
<211> LENGTH: 32
<212> TYPE: DNA
<213> ORGANISM: Rice Tungro Baciliform Virus

<400> SEQUENCE: 17
cggaattctg atccaaagat aaaggaacaa ag                                  32

<210> SEQ ID NO 18
<211> LENGTH: 33
<212> TYPE: DNA
<213> ORGANISM: Rice Tungro Baciliform Virus

<400> SEQUENCE: 18
cggaattcaa gcatcaataa aagaagactg aag                                 33

<210> SEQ ID NO 19
<211> LENGTH: 35
<212> TYPE: DNA
<213> ORGANISM: Rice Tungro Baciliform Virus

<400> SEQUENCE: 19
```

-continued cggaattcgg aatccacttt aaattattgt acctc                           35

<210> SEQ ID NO 20
<211> LENGTH: 36
<212> TYPE: DNA
<213> ORGANISM: Rice Tungro Bacilliform Virus

<400> SEQUENCE: 20
cggaattctg taagagtgtg taaaatctag cctacc                          36

<210> SEQ ID NO 21
<211> LENGTH: 34
<212> TYPE: DNA
<213> ORGANISM: Rice Tungro Bacilliform Virus

<400> SEQUENCE: 21
cggaattcct atataaggag aagtagtctg catg                            34

<210> SEQ ID NO 22
<211> LENGTH: 34
<212> TYPE: DNA
<213> ORGANISM: Rice Tungro Bacilliform Virus

<400> SEQUENCE: 22
cggaattcgg agaagtagtc tgcatgtaat aggc                            34

<210> SEQ ID NO 23
<211> LENGTH: 35
<212> TYPE: DNA
<213> ORGANISM: Rice Tungro Bacilliform Virus

<400> SEQUENCE: 23
aactgcagtc aatatttgag aaagtaagat ccctc                           35

<210> SEQ ID NO 24
<211> LENGTH: 33
<212> TYPE: DNA
<213> ORGANISM: Rice Tungro Bacilliform Virus

<400> SEQUENCE: 24
aactgcagta agatccctct tcagaacata tgt                             33

<210> SEQ ID NO 25
<211> LENGTH: 30
<212> TYPE: DNA
<213> ORGANISM: Rice Tungro Bacilliform Virus

<400> SEQUENCE: 25
aactgcagaa catcgctctg ataccagatg                                 30

<210> SEQ ID NO 26
<211> LENGTH: 30
<212> TYPE: DNA
<213> ORGANISM: Rice Tungro Bacilliform Virus

<400> SEQUENCE: 26
aactgcagcg tgatgaggaa gagctacttg                                 30

<210> SEQ ID NO 27
<211> LENGTH: 27
<212> TYPE: DNA
<213> ORGANISM: Rice Tungro Bacilliform Virus

<400> SEQUENCE: 27

-continued

```
aactgcagct tgttcccttg gcatcac                                    27

<210> SEQ ID NO 28
<211> LENGTH: 28
<212> TYPE: DNA
<213> ORGANISM: Rice Tungro Bacilliform Virus

<400> SEQUENCE: 28
aactgcagca gcggataagt tcttgatg                                   28

<210> SEQ ID NO 29
<211> LENGTH: 31
<212> TYPE: DNA
<213> ORGANISM: Rice Tungro Bacilliform Virus

<400> SEQUENCE: 29
aactgcagca gctaatcctt ctttgaagag g                               31

<210> SEQ ID NO 30
<211> LENGTH: 31
<212> TYPE: DNA
<213> ORGANISM: Rice Tungro Bacilliform Virus

<400> SEQUENCE: 30
aactgcagct cttctcttgc tcttgtggaa g                               31

<210> SEQ ID NO 31
<211> LENGTH: 28
<212> TYPE: DNA
<213> ORGANISM: Rice Tungro Bacilliform Virus

<400> SEQUENCE: 31
aactgcagct ctgggtgtgt ggatttcg                                   28
```

RTBV PLANT PROMOTER AND PROCESS THEREOF

TECHNICAL FIELD

The present invention relates to isolation of novel nucleotide sequences from rice tungro bacilliform virus (RTBV) showing promoter activity in transgenic plants. It further relates to the characterization of the functional domains in the RTBV promoter wherein the promoter sequences function in a constitutive or a tissue specific manner to drive the expression of the heterologous nucleic acid sequences in both monocot and dicot plants, cells and tissues.

BACKGROUND INFORMATION AND PRIOR ART

Rice is considered to be the most important food crop in the world as it is the primary source of dietary calories to majority of human beings. To continue providing adequate calories and to improve the quality of rice-based food in the coming years for the growing population of rice-eaters, the rice plant has to be improved in order to increase yields by exploiting hybrid vigor, to withstand unfavorable conditions like pests, diseases, drought, flooding, salinity and extreme temperatures and to incorporate added nutrients. For a majority of these improvements, genes taken from other organisms, commonly known as transgenes, have to be introduced and expressed in rice.

From agronomic point of view, to generate superior rice varieties, multiple genes conferring desirable genetic traits need to be introduced into the same transgenic background. Accomplishing gene pyramiding, however, is not as easy.

In order to ensure stable expression of the transgenes, they have to be fused to specific DNA elements known as promoters, which function as controlling units for the generation of mRNA from genes, the most important stage of gene expression. These sequences are essentially regulatory in nature, in the sense they initiate the process of transcription and may regulate the rate of transcription. A relatively small number of promoters have been commonly used for expressing transgenes in plants. Additionally, the number of promoters which can drive high levels of constitutive expression in both dicot and monocot plants are even fewer. Also, there are just a handful of promoters driving tissue- or organ-specific expression. The current scientific challenge therefore, lies in the identification of novel regulatory elements to introduce greater versatility in terms of attaining desired spatio-temporal mRNA expression patterns.

Studies have shown that using the same promoter to drive the expression of two distinct heterologous genes in the same plant can lead to gene silencing. This problem can, however, be circumvented by using different promoters for each of the heterologous gene. Hence, there is a need for identifying new promoters which can show tissue- and/or development-specific expression, and can be used for transgene expression in various plants. This document provides such information on a new promoter identified and characterized from the rice tungro bacilliform virus (RTBV), isolated and modified from virus infected rice plants growing in fields in West Bengal, India.

The Cauliflower mosaic virus 35S promoter (CaMV 35S) and its derivatives are among the most commonly used promoters for this purpose. The CaMV 35S is active in dicots, but its relative strength is substantially lower in monocots than in dicots. Other dicot promoters have also been used for monocot transformation, but activity tends to be lower for monocot promoters (Wilmink et al., 1995). Several promoters have been identified to drive a high level of transgene expression in monocots, for example, the rice Act1 promoter (McElroy et al., 1991), the rice rbcs promoter (Kyozuka et al., 1993), the maize Ubi1 promoter (Toki et al., 1992; Cornejo et al., 1993) and the rice cytochrome C gene promoter OsCc1 (Jang et al., 2002). Of these, only the CaMV 35S (Terada and Shimamoto, 1990), rice Act1, maize Ubi1 and rice OsCc1 are constitutive in nature. Only a few tissue-specific promoters have been identified in rice. For example, rice seed storage protein glutelin (Gt1) promoter has been used to express transgenes in rice seeds (Ye et al., 2000) and rice Glu-B1 promoter has been used for endosperm-specific expression of soybean ferritin gene (Goto et al., 1999). Some of the other characterized promoters in rice include, the potato pin2 promoter which has been shown to be wound inducible (Xu et al., 1993), the maize Adh1 promoter which is strongly induced in roots under anaerobic conditions (Kyozuka et al., 1991) and the maize pep and rbcS promoters which are mesophyll specific (Matsuoka et al., 1994).

Beachy, Roger N. and Bhattacharyya, Maitrayee have identified and characterized a promoter from RTBV, isolated from Philippines (U.S. Pat. No. 5,824,857). The utility of the promoter was implicated in driving vascular specific expression in transgenic plants. However, the present study deals with the identification and characterization of a promoter fragment from RTBV, isolated from West Bengal, India, which has no significant homology to the previously-characterized RTBV promoter. The DNA sequence of this full-length clone has been deposited in the EMBL Sequence Database and has been assigned the following accession number: AJ314596, but no function to the DNA sequences was assigned earlier. The present invention deals with the identification of new promoters from RTBV (West Bengal isolate) and their use for transgene expression in plants.

OBJECTS OF INVENTION

The main object of the present invention is to provide an isolated promoter from rice tungro bacilliform virus (RTBV), having nucleotide sequences as shown in SEQ ID NO: 1 in the Sequence Listing.

Another object of the present invention is to provide deleted versions of RTBV promoter having SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14 and SEQ ID NO: 15 as shown in the Sequence Listing.

Another object of the present invention is to provide a chimeric plant transformation vector comprising the RTBV promoter (full length, FL) or its deleted versions UD1, UD2, UD3, UD4, UD5 and UD6 (upstream deletions, UD) and DD1, DD2, DD3, DD4, DD5, DD6, DD7 and DD8, (downstream deletions, DD) operably linked to heterologous nucleic acid sequence of interest.

Yet another object of the invention is to provide a chimeric plant transformation vector, wherein the heterologous nucleic acid sequence encodes a polypeptide capable of conferring improved agronomic traits or resistance to diseases or insects to a plant which is operably linked to the RTBV promoter and its derivatives described above.

Yet another object of the present invention is to provide plant cells, tissues, organs and plants (monocots or dicots) transformed with various RTBV promoter sequences (SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14 and SEQ ID NO: 15) fused to heterologous nucleic acid sequences. Still another object of the invention is to provide a method of expression of one or more heterologous nucleic acid sequence of interest under the regulatory control of RTBV (FL) or upstream deletions (UD1, UD2, UD3, UD4, UD5, UD6) or downstream deletions (DD1, DD2, DD3, DD4, DD5, DD6, DD7 and DD8) promoter sequences.

Still another object of present invention is to provide a method for production of transgenic monocot or dicot plants expressing heterologous nucleic acid sequences under the control of RTBV (FL) or upstream deletions (UD1, UD2, UD3, UD4, UD5, UD6) or downstream deletions (DD1, DD2, DD3, DD4, DD5, DD6, DD7 and DD8) promoter sequences.

SUMMARY OF INVENTION

The present invention relates to isolation of novel nucleotide sequences from rice tungro bacilliform virus (RTBV) showing promoter activity in plants. The nucleic acid sequences provided herein (isolated from RTBV) direct the expression of operably linked nucleotide sequences in cells, tissues and organs of both monocot and dicot plants.

The invention provides RTBV promoter (FL, 876 bp) having nucleotide sequences as shown in SEQ ID NO: 1 (Sequence Listing). Also, the present invention provides deleted versions of RTBV promoters which are UD1 (818 bp, SEQ ID NO: 2); UD2 (789 bp, SEQ ID NO: 3); UD3 (754 bp, SEQ ID NO: 4); UD4 (718 bp, SEQ ID NO: 5); UD5 (681 bp, SEQ ID NO: 6); UD6 (671 bp, SEQ ID NO: 7); DD1 (862 bp, SEQ ID NO: 8); DD2 (793 bp, SEQ ID NO: 9); DD3 (691 bp, SEQ ID NO: 10); DD4 (581 bp, SEQ ID NO: 11); DD5 (426 bp, SEQ ID NO: 12); DD6 (325 bp, SEQ ID NO: 13); DD7 (289 bp, SEQ ID NO: 14) and DD8 (254 bp, SEQ ID NO: 15)

The present invention further relates to the analysis of the functional domains of RTBV promoters as shown in SEQ ID NO: 1, by fusing full-length and deleted versions of the RTBV sequences with the bacterial reporter gene GUS and to study the expression of the reporter gene in various tissues of transgenic rice and tobacco plants during different development stages.

In the preferred embodiment promoter sequences from RTBV, specified as FL, 876 bp in length, as shown in SEQ ID NO: 1, the upstream deletion of FL such as UD1, UD2, UD3, UD4, UD5 and UD6 as shown in SEQ ID NO: 2, SEQ ID NO: 3, SEQ ID NO: 4, SEQ ID NO: 5, SEQ ID NO: 6 and SEQ ID NO: 7, respectively, were identified. Further, the downstream deletions of FL sequences such as DD1, DD2, DD3, DD4, DD5, DD6, DD7 and DD8 as shown in SEQ ID NO: 8, SEQ ID NO: 9, SEQ ID NO: 10, SEQ ID NO: 11, SEQ ID NO: 12, SEQ ID NO: 13, SEQ ID NO: 14 and SEQ ID NO: 15, respectively, were identified. These sequences were used to drive the expression of bacterial reporter GUS gene in rice and tobacco plants, cells, tissues and organs.

The present invention also relates to RTBV promoter and its deletions which function in a constitutive or tissue specific manner to drive the expression of the heterologous nucleic acid sequences in monocot and dicot plants, cells, organs and tissues.

Another aspect of the present invention is to provide RTBV full-length promoter (FL) and its upstream and downstream deletions which express in a tissue-specific manner predictably (FL, UD1, UD2, UD3, UD4, UD5, DD3 and DD4) or constitutively (DD7 and DD8) in rice.

Another aspect of the invention involves constructing a chimeric plant transformation vector comprising the FL, upstream and downstream deletion promoter sequences fused to heterologous nucleic acid sequences of interest.

The present invention further provides a method for generating transgenic plants (monocot or dicot) by introducing a chimeric plant transformation vector into plant cells wherein the chimeric plant transformation vector comprises RTBV promoter sequences (either FL or upstream or downstream deletions) fused to a heterologous structural gene.

The present invention also provides a method for expression of heterologous nucleic acid sequences in a transgenic plant under the regulatory control of said RTBV promoter sequences (either FL or upstream or downstream deletion) wherein the said heterologous nucleic acid sequence carries out functions capable of conferring improved agronomic traits or resistance to diseases, or insects to a plant.

The present invention also provides for a method for expression of heterologous gene in a transgenic plant under the regulatory control of said RTBV promoter sequences (either FL or upstream or downstream deletion promoter mutants) wherein the plant is a monocot for example rice, wheat or maize.

The present invention also provides for a method for expression of heterologous nucleic acid sequences in a transgenic plant under the regulatory control of said RTBV promoter sequences (either FL or upstream or downstream deletion mutants) wherein the plant is dicot for example tobacco, cotton or tomato.

The present invention also provides plants, cells or tissues comprising of RTBV promoter and heterologous nucleic acid sequences under the control of RTBV (FL) or upstream deletions (UD1, UD2, UD3, UD4, UD5 and UD6) or downstream deletions (DD1, DD2, DD3, DD4, DD5, DD6, DD7 and DD8) promoter sequences.

BRIEF DESCRIPTION OF ACCOMPANYING DRAWINGS

FIG. 1: The full-length RTBV promoter sequence with SEQ ID NO: 1 showing the positions of forward primers (FP) or reverse primers (RP) employed for PCR amplification.

FIG. 2: Schematic representation of PCR generated RTBV promoter deletion fragments.

FIG. 3: Schematic representation of the T-DNA region of the promoter-less vector, pCAMBIA1381z FIG. 4: Sections of transgenic rice tissues showing GUS activity with various constructs.

DETAILED DESCRIPTION OF THE PREFERRED EMBODIMENTS

A preferred embodiment of the present invention relates to isolation and characterization of a promoter from rice tungro bacilliform virus (RTBV), capable of directing expression of operably linked nucleic acid sequences in monocot and dicot plant cells, tissues and organs, having nucleotide sequences as shown in SEQ ID NO: 1.

Another embodiment of the present invention relates to providing deleted versions (UD1, UD2, UD3, UD4, UD4, UD5, UD6, DD1, DD2, DD3, DD4, DD5, DD6, DD7 and DD8) of the RTBV promoter comprising at least 59-876 bp (UD1) of SEQ ID NO: 1 as shown in SEQ ID NO: 2. The nomenclature and sequence ID of the various deleted versions of RBTV promoter is given as follows: UD2 (88-876 bp of SEQ ID NO: 1) as shown in SEQ ID NO: 3. UD3 (123-876 bp of SEQ ID NO: 1) as shown in SEQ ID NO: 4. UD4 (159-876 bp of SEQ ID NO: 1) as shown in SEQ ID NO: 5. UD5 (196-876 bp of SEQ ID NO: 1) as shown in SEQ ID NO: 6. UD6 (206-876 bp of SEQ ID NO: 1) as shown in SEQ ID NO: 7. DD1 (1-862 bp of SEQ ID NO: 1) as shown in SEQ ID NO: 8. DD2 (1-793 bp of SEQ ID NO: 1) as shown in SEQ ID NO: 9. DD3 (1-691 bp of SEQ ID NO: 1) as shown in SEQ ID NO: 10. DD4 (1-581 bp of SEQ ID NO: 1) as shown in SEQ ID NO: 11. DD5 (1-426 bp of SEQ ID NO: 1) as shown in SEQ ID NO: 12, DD6 (1-325 bp of SEQ ID NO: 1) as shown in SEQ ID NO: 13. DD7 (1-289 bp) of SEQ ID NO: 1 as shown in SEQ ID NO: 14. DD8 (1-254 bp) of SEQ ID NO: 1 as shown in SEQ ID NO: 15.

Another embodiment of the present invention relates to providing FL and its upstream and downstream deletions which express in a tissue-specific manner predictably (UD1, UD2, UD3, UD4, UD5, DD3 and DD4) or constitutively (DD7 and DD8) in rice.

Another embodiment of the present invention relates to providing a chimeric plant transformation vector comprising the RTBV promoter (FL, UD1, UD2, UD3, UD4, UD5, UD6, DD1, DD2, DD3, DD4, DD5, DD6, DD7 and DD8) which is operably linked to a heterologous nucleic acid sequence of interest.

Yet another preferred embodiment of the present invention relates to generation of chimeric plant transformation vector comprising said RTBV promoters (FL, UD1, UD2, UD3, UD4, UD5, UD6, DD1, DD2, DD3, DD4, DD5, DD6, DD7 and DD8) linked to a heterologous gene encoding a polypeptide which is capable of conferring improved agronomic traits or resistance to diseases, or insects to a plant.

Still another embodiment of the present invention relates to providing transformed plant cells, tissues and organs in monocot and dicot plants.

Yet another embodiment of the present invention relates to providing a transgenic plant wherein the said plant is from the Graminae family such as rice, wheat and maize.

Yet another embodiment of the present invention relates to providing a transgenic plant wherein the said plant is dicot such as tobacco, cotton and tomato.

Yet another embodiment of the present invention relates to providing a method of expression of one or more heterologous nucleic acid sequence of interest comprising RTBV (FL, UD1, UD2, UD3, UD4, UD5, UD6, DD1, DD2, DD3, DD4, DD5, DD6, DD7 and DD8) promoter, wherein the said method comprises the steps of:
(a) Generating a chimeric plasmid DNA construct (plant transformation vector) comprising the promoter sequences as shown in either SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14 or SEQ ID NO: 15 which are operably linked to a heterologous nucleic acid sequence of interest.
(b) Introducing a plasmid from step (a) to a suitable host cell.
(c) Transforming the plant cells or tissues using the cells of step (b) to generate a transgenic plant expressing the said heterologous nucleic acid sequence.

Yet another embodiment of the present invention relates to a method of expression wherein the said heterologous nucleic acid sequence encodes a polypeptide capable of conferring improved agronomic traits to a plant.

Still another embodiment of the present invention relates to providing a method of expression wherein the said heterologous nucleic acid sequence encodes a polypeptide capable of conferring improved agronomic traits or resistance to disease or insects to a plant wherein the said transgenic plant is a monocot.

Yet another embodiment of the present invention relates to a method of expression wherein the said heterologous nucleic acid sequence encodes a polypeptide capable of conferring improved agronomic traits or resistance to disease or insects to a plant wherein the said transgenic plant is from the Graminae family, for example, rice.

Yet another embodiment of the present invention relates to a method of expression wherein the said heterologous nucleic acid sequence encodes a polypeptide capable of conferring improved agronomic traits or resistance to disease or insects to a plant wherein the said transgenic plant is a dicot, such as tobacco.

The DNA of RTBV (West Bengal isolate) was purified as given in Example 1. A fragment of the above DNA was characterized for promoter activity. Various upstream and downstream deletions were carried out on the above promoter fragment for analysis of promoter activity and the details are given in Example 2.

The complete sequence of the RTBV promoter is shown in FIG. 1. The primers have been indicated on top of the 5' base, in case of forward primer or 3' base in case of reverse primer. The various deletions obtained for RTBV FL promoter is schematically represented in FIG. 2. The forward primers are represented as FP1 to FP7 and reverse primers as RP1 to RP9. The rectangular box depicts a ~900 bp section of RTBV genome. The arrowheads denote approximate primer position and the horizontal line joining them, the expected PCR fragments (see FIG. 2).

The FL RTBV promoter sequence (876 bp, SEQ ID NO: 1) was amplified by employing oligonucleotide primers FP1 (SEQ ID NO: 16) and RP1 (SEQ ID NO: 23). The FL fragment was used for generating both its 5' and 3' promoter deletion fragments. The 5' deletion fragments are UD1, UD2, UD3, UD4, UD5 and UD6. The 3' deletion fragments are DD1, DD2, DD3, DD4, DD5, DD6, DD7 and DD8. The UD1 fragment (818 bp, SEQ ID NO: 2) was amplified using primers FP2 (SEQ ID NO: 17) and RP1 (SEQ ID NO: 23). The UD2 fragment (789 bp, SEQ ID NO: 3) was amplified using primers FP3 (SEQ ID NO: 18) and RP1. The UD3 fragment (754 bp, SEQ ID NO: 4) was amplified using primers FP4 (SEQ ID NO: 19) and RP1. The UD4 fragment (718 bp, SEQ ID NO: 5) was amplified using primers FP5 (SEQ ID NO: 20) and RP1. The UD5 fragment (681 bp, SEQ ID NO: 6) was amplified using primers FP6 (SEQ ID NO: 21) and RP1. The UD6 fragment (671 bp, SEQ ID NO: 7) was amplified using primers FP7 (SEQ ID NO: 22) and RP1.

The DD1 deletion fragment (862 bp, SEQ ID NO: 8) was amplified by employing primers FP1 (SEQ ID NO: 16) and RP2 (SEQ ID NO: 24). The DD2 deletion fragment (793 bp, SEQ ID NO: 9) was amplified using primers FP1 and RP3 (SEQ ID NO: 25). The DD3 deletion fragment (691 bp, SEQ ID NO: 10) was amplified using primers FP1 and RP4 (SEQ ID NO: 26). The deletion fragment DD4 (581 bp, SEQ ID NO: 11) was amplified using primers FP1 and RP5 (SEQ ID NO: 27). The deletion fragment DD5 (426 bp, SEQ ID NO: 12) was amplified using primers FP1 and RP6 (SEQ ID NO: 28). The deletion fragment DD6 (325 bp, SEQ ID NO: 13) was amplified using primers FP1 and RP7 (SEQ ID NO: 29). The deletion fragment DD7 (289 bp, SEQ ID NO: 14) was amplified using primers FP1 and RP8 (SEQ ID NO: 30). The deletion fragment DD8 (254 bp, SEQ ID NO: 15) was amplified using primers FP1 and RP9 (SEQ ID NO: 31). The details of various deletion fragments, their sizes, the primers employed to generate these fragments and their SEQ ID numbers are provided in Table 1.

The various DNA fragments were cloned in promoter-less plant transformation vector backbone such as pCAMBIA1381z to drive the expression of GUS gene with intron. The schematic representation of the T-DNA region between the left and right border of plant transformation vector pCAMBIA1381z is shown in FIG. 3. The promoterless vector, pCAMBIA1381z was used with hygromycin resistance marker gene for cloning in rice or with kanamycin resistance marker gene for cloning in tobacco. Various chimeric plant transformation vectors having pCAMBIA1381z backbone were obtained, each having different DNA fragments namely FL, UD1, UD2, UD3, UD4, UD5, UD6, DD1, DD2, DD3, DD4, DD5, DD6, DD7 and DD8 upstream of the GUS (intron) gene. These vector constructs were mobilized into *Agrobacterium* strain EHA105 as given in Example 3. The *Agrobacterium* strain was used to transform plants such as tobacco and rice. The transformation of rice was carried out as given in Example 4. The transformation of tobacco was carried out as given in Example 5. The transformed plants were subsequently analyzed for GUS activity using standard procedure which is given in Example 6.

The expression patterns of the promoter activity in rice was studied for the 876 base pair full-length (FL) promoter as shown in SEQ ID NO: 1, as well as the upstream deletion promoter mutants UD1, UD2, UD3, UD4 and UD5 as shown in SEQ ID NO: 2, SEQ ID NO: 3, SEQ ID NO: 4, SEQ ID NO: 5 and SEQ ID NO: 6, respectively. The downstream deletion mutants DD3, DD4, DD5, DD6, DD7 and DD8 as shown in SEQ ID NO: 10, SEQ ID NO: 11, SEQ ID NO: 12, SEQ ID NO: 13, SEQ ID NO: 14 and SEQ ID NO: 15, respectively, were identified and used for analyzing the expression of bacterial reporter GUS gene in rice. The GUS activity of hand-cut transformed rice tissue is shown in FIG. 4, the blue color typically revealing promoter activity.

The FL promoter as shown in SEQ ID NO:1, upstream deletion promoter fragments UD1, UD2, UD3, UD4 and UD5 as shown in SEQ ID NO: 2, SEQ ID NO: 3, SEQ ID NO: 4, SEQ ID NO: 5 and SEQ ID NO: 6 respectively, as well as downstream deletion mutants DD5, DD6, DD7 and DD8 as shown in SEQ ID NO: 12, SEQ ID NO: 13, SEQ ID NO: 14 and SEQ ID NO: 15 were employed to transform tobacco plants and tissues to drive the expression of bacterial reporter GUS gene. The GUS activity of transformed tobacco tissues was analyzed to study the expression in various tissues.

In rice, the FL (SEQ ID NO: 1) promoter fragment showed strong constitutive expression of reporter gene activity in all cells of shoot and root except the epidermis and root tips at 7 days post germination (dpg). The expression decreased gradually with the age of tissue, persisting strongly in the vascular tissues like phloem and the bundle sheath at 30 dpg. The expression became weak to negligible by 100 dpg. A similar expression pattern was seen for the constructs UD1, UD2, UD3, UD4, UD5, DD3 and DD4. In two of its downstream deleted versions, DD7 and DD8, however, a second pattern of expression was observed. In these two constructs, the promoter activity was constitutive for the entire life of plant except the epidermis and root tips, where there was no expression. Another set of downstream deletion constructs DD5 and DD6 displayed a third pattern of expression, where there was no visually detectable GUS activity at any developmental stage of the plants. The expression patterns of FL and its various deletion fragments of RTBV promoters in young shoot and mature leaf explants of rice are shown in FIG. 4.

In rice, in the inflorescence, palea and lemma displayed GUS activity only in the conducting tissues for FL, UD1, UD2, UD3, UD4, UD5, DD3 and DD4, whereas, in the DD7 and DD8 it was detectable in the inter-veinal tissues also. In all these constructs, the filament and connective tissue of the stamens showed promoter activity but the anther lobes and pollens did not. In gynoecium, the promoter activity was limited to the feathery stigma and bifid style but none in the ovary.

GUS activity estimates in young leaf tissues of second-generation of transgenics (T1) in rice suggested that the RTBV promoter is comparable to the well-established Maize Ubi1 as well as the CaMV 35S promoter in the degree of expression, the values being comparable at ~25,000 nmol of 4-MU (4-Methylumbelliferone) per mg protein per hour.

RTBV promoter was also found to be active in a heterologous system like tobacco, but unlike RTBV promoter transgenic rice, the expression from FL, UD1, UD2, UD3, UD4, DD5, DD6, DD7 and DD8 was limited to the vasculature in stem, leaves and roots even in young tissues, a pattern true for mature FL rice transgenics. Whereas, in DD7 and DD8, only the cotyledonary leaves expressed GUS activity constitutively, the expression then got restricted to the vascular tissues as the plant matured. No expression was seen in any tissue in UD5, unlike rice. No distinct difference was observed in the expression profiles in flowers in FL, UD or DD, the expression being limited to vascular tissues in sepals and petals. No promoter activity was observed in either the androecium or the gynoecium of any of the constructs.

In transgenic rice plants, phloem-specific activity of full-length RTBV promoter from Philippines is reported earlier (Bhattacharyya-Pakrasi et al., 1993; Yin and Beachy, 1995; Yin et al., 1997), but the promoter sequence identified was from a different isolate (Philippines) than the present study (West Bengal, India). Later, upon inclusion of 278 nucleotides of downstream promoter sequences (dps), the same RTBV promoter was reported to show activity in a wider range of cells than previously observed in the absence of dps (Klöti et al., 1999). The promoter activity was detected mainly in young tissues which was gradually lost with increasing age of plant.

In the present study, the 3' deletions (DD7 and DD8) describe a promoter sequence which constitutively expresses the heterologous gene in all the tissues for the entire life of the rice plant. Such activity has not been reported earlier for RTBV promoter rice transgenics. In all the previously-reported RTBV promoters, the activity of the full-length promoter decreased with age of the plant and became very low at an older age, getting restricted to the vascular tissues. In contrast, some of the promoter constructs reported here (DD7 and DD8) remained active even in mature plants. In FL, UD1, UD2, UD3, UD4, UD5, DD3 and DD4, the expression pattern was similar to that described by Klöti et al., (1999). In addition, the tissue-specificity of the present promoter was also different from the previously-reported RTBV promoters in another way; two constructs, corresponding to DD5 and DD6 showed no expression in the entire life of the plant. The results are indicative of presence of certain positive and negative elements which in conjunction with cellular trans-acting factors determine the strength and tissue specificity of the promoter. Thus, it is felt that the activity of the promoters described here will be very useful in expressing transgenes in a predictable tissue-specific manner (FL, UD1, UD2, UD3, UD4, UD5, DD3 and DD4) or constitutively (DD7 and DD8) in rice. The expression in tobacco plants, however, was tissue-limited, the activity being limited to vascular tissues. These, differential expression patterns indicate that different proteins are interacting with the same chimeric DNA sequence (RTBV promoter) in different plant systems. The expression patterns are summarized in Table 2.

EXAMPLES

The examples given are merely illustrative of the uses, processes and products claimed in this invention, and the practice of the invention itself is not restricted to or by the examples described.

Example 1

DNA Extraction and Identification of Promoters

Virus-infected material was collected from experimental farms of Bidhan Chandra Krishi Viswavidyalaya, Kalyani, West Bengal, India. RTBV DNA was isolated using a crude virus preparation, according to the method of Jones et al., (1991).

The viral DNA was then digested to completion with a number of restriction enzymes and cloned in pUC19 using standard procedures. A combination of nested deletions and primer walking was utilized to derive the complete sequence of a full-length RTBV clone, which was a BamHI clone (Nath et al., 2002). The DNA sequence of the full-length clone has been deposited in the EMBL Sequence Database and has been assigned the following accession number: AJ314596.

Example 2

Promoter Analysis

The complete sequence of the RTBV full length promoter (SEQ ID NO: 1) is shown in FIG. 1, and the primer numbers used for generating the various promoter variants by PCR have been indicated on top of the 5' end (forward primer) or 3' end (reverse primer).

The full sequence of all the primers, RTBV (FL) and RTBV deletion (UD and DD) sequences are also provided as a Sequence Listing through Patent-In Software.

The sequences of the set of primers synthesized for the full-length (876 bp) construct are as follows:

```
FP1
                                    (SEQ ID NO: 16)
5'-CGGAATTCTGTCCTGCACCACCTCAATG-3'

RP1
                                    (SEQ ID NO: 23)
5'-AACTGCAGTCAATATTTGAGAAAGTAAGATCCCTC-3'.
```

For the 3' deletion DD1 (862 bp) construct, the forward primer, FP1 is the same but the reverse primer sequence is as follows:

```
RP2
                                    (SEQ ID NO: 24)
5'-AACTGCAGTAAGATCCCTCTTCAGAACATATGT-3'.
```

For the 3' deletion DD2 (793 bp) construct, the Forward primer, FP1 is the same but the reverse primer sequence is as follows:

```
RP3
                                    (SEQ ID NO: 25)
5'-AACTGCAGAACATCGCTCTGATACCAGATG-3'
```

For the 3' deletion DD3 (691 bp) construct, the Forward primer, FP1 is the same but the reverse primer sequence is as follows:

```
RP4
                                    (SEQ ID NO: 26)
5'-AACTGCAGCGTGATGAGGAAGAGCTACTTG-3'
```

For the 3' deletion DD4 (581 bp) construct, the Forward primer, FP1 is the same but the reverse primer sequence is as follows:

```
RP5
                                    (SEQ ID NO: 27)
5'-AACTGCAGCTTGTTCCCTTGGCATCAC-3'
```

For the 3' deletion DD5 (426 bp) construct, the Forward primer, FP1 is the same but the reverse primer sequence is as follows:

```
RP6
                                    (SEQ ID NO: 28)
5'-AACTGCAGCAGCGGATAAGTTCTTGATG-3'
```

For the 3' deletion DD6 (325 bp) construct, the Forward primer, FP1 is the same but the reverse primer sequence is as follows:

```
RP7
                                    (SEQ ID NO: 29)
5'-AACTGCAGCAGCTAATCCTTCTTTGAAGAGG-3'
```

For the 3' deletion DD7 (289 bp) construct, the Forward primer, FP1 is the same but the reverse primer sequence is as follows:

```
RP8
                                    (SEQ ID NO: 30)
5'-AACTGCAGCTCTTCTCTTGCTCTTGTGGAAG-3'
```

For the 3' deletion DD8 (254 bp) construct, the Forward primer, FF1 is the same but the reverse primer sequence is as follows:

```
RP9
                                    (SEQ ID NO: 31)
5'-AACTGCAGCTCTGGGTGTGTGGATTTCG-3'
```

For the 5' deletion UD1 (818 bp) construct, the Reverse primer, RP1 is the same but the forward primer sequence is as follows:

```
FP2
                                    (SEQ ID NO: 17)
5'-CGGAATTCTGATCCAAAGATAAAGGAACAAAG-3'
```

For the 5' deletion UD2 (789 bp) construct, the Reverse primer, RP1 is the same but the forward primer sequence is as follows:

```
FP3
                                    (SEQ ID NO: 18)
5'-CGGAATTCAAGCATCAATAAAAGAAGACTGAAG-3'
```

For the 5' deletion UD3 (754 bp) construct, the Reverse primer, RP1 is the same but the forward primer sequence is as follows:

FP4
(SEQ ID NO: 19)
5'-CG<u>GAATTC</u>GGAATCCACTTTAAATTATTGTACCTC-3'

For the 5' deletion UD4 (718 bp) construct, the Reverse primer, RP1 is the same but the forward primer sequence is as follows:

FP5
(SEQ ID NO: 20)
5'-CG<u>GAATTC</u>TGTAAGAGTGTGTAAAATCTAGCCTACC-3'

For the 5' deletion UD5 (681 bp) construct, the Reverse primer, RP1 is the same but the forward primer sequence is as follows:

FP6
(SEQ ID NO: 21)
5'-CG<u>GAATTC</u>CTATATAAGGAGAAGTAGTCTGCATG-3'

For the 5' deletion UD6 (671 bp) construct, the Reverse primer, RP1 is the same but the forward primer sequence is as follows:

FP7
(SEQ ID NO: 22)
5'-CG<u>GAATTC</u>GGAGAAGTAGTCTGCATGTAATAGGC-3'

In all the primer sequences, the EcoRI and Pst I enzyme sites are underlined. The complete sequence of the RTBV full length promoter is shown in FIG. 1. The primer numbers used to generate the different promoter variants have been indicated on top of the 5' end (forward primer) or 3' end (reverse primer). DNA from cloned RTBV DNA was used as a template to amplify the promoter fragments using the Hi-Fidelity Taq DNA Polymerase (Roche Applied Science, Germany) under the following conditions: an initial denaturation at 94° C. for 5 minutes, followed by 10 cycles of 94° C. heat denaturation for 30 seconds, 58° C. annealing for 30 seconds and 72° C. of extension for 1 minute, followed by 25 cycles of, 94° C. heat denaturation for 30 seconds, 58° C. annealing for 30 seconds and 72° C. of extension for 1 minute and additional 5 seconds increment for each extension per cycle, finally a 7 minutes extension was given. The PCR fragments were purified by PCR purification kit (Qiagen, Germany), digested over night using the restriction enzymes EcoRI and PstI followed by cloning in EcoRI and PstI digested promoter-less plant transformation vector, pCAMBIA1381z, having GUS reporter gene (with catalase intron) and hygromycin-resistance as selectable marker. Since hygromycin resistance can not be used effectively for selecting transformants in tobacco, the hygromycin-resistance gene from the promoter-less vector, pCAMBIA1381z was excised with restriction enzyme XhoI, and an XhoI fragment specifying kanamycin-resistance gene from pCAMBIA2300 was introduced into the vector. T-DNA region of the promoter-less vector is shown in FIG. 3.

The different deleted promoter fragments were eluted and ligated with the newly constructed vector backbone to generate a series of RTBV promoter deletion constructs for tobacco transformation, using kanamycin as the selectable marker. Schematic representation of PCR generated RTBV promoter deletion fragments are shown in FIG. 2.

Example 3

Transformation of Binary Vectors/Constructs in to *Agrobacterium*

These chimeric plant transformation vectors were mobilized into *Agrobacterium* strain EHA105 by the freeze-thaw method (An et al. 1988). Approximately 1 μg plasmid DNA was mixed with competent *Agrobacterium* cells, and then frozen in liquid nitrogen, this was followed by incubation at 37° C. for 5 minutes. To these transformed cells was added 1 ml Luria Bertani (LB) broth and the contents were incubated at 28° C. for 4-5 hours. The bacterial suspension was subsequently pelleted and spread on LB agar plate containing appropriate antibiotics. The plates were kept 28° C. for 2 days and single colonies were analysed for presence of correct construct by standard protocols.

Example 4

Transformation in Rice

Scutellar derived calli from rice variety PB1, sub-cultured for one and a half months in dark on callus induction medium, CIM [$N_6B_5$ medium (Chu, 1978; Gamborg et al., 1968) containing 2 mg/l 2,4-D (2,4-Dichlorophenoxyacetic acid) and solidified by 0.8% agar] at 28° C. were subjected to *Agrobacterium* mediated transformation according to the protocol of Wang et al., (1997). Rice calli were infected with a suspension of *Agrobacterium* cells in liquid $N_6B_5$ medium having 100 μM acetosyringone and 2 mg/l 2,4-D and at a final cell density of $2\times10^8$ cells/ml for twenty minutes. The calli were then put on co-cultivation medium (CIM having 100 μM acetosyringone) at 28° C. for two and a half days in dark. Washes were given with a bacteriostatic agent, augmentin at 150 mg/l and calli placed on selection medium (CIM containing 30 mg/l hygromycin and 150 mg/l augmentin) in dark for one to one and a half months. Cream-coloured putative transformed calli were further kept on selection plates for five to six days before shifting to pre-regeneration medium ($N_6B_5$ medium containing 0.5 mg/l benzyl amino purine [BAP], 10 μM abscissic acid, 30 mg/l hygromycin and 150 mg/l augmentin) for a week, the incubation being three days in dark and four days in light. The calli were then shifted to regeneration medium ($N_6B_5$ medium containing 1 mg/l BAP, 30 mg/l hygromycin and 150 mg/l augmentin) till plantlets started to emerge. These were subsequently shifted to culture tubes containing regeneration medium. To ensure a well developed root system (hardening), putative transgenics were shifted to liquid MS (Murashige and Scoog, 1962) medium and ultimately planted in pots containing soilrite and soil in 1:1 ratio and transferred to green house till maturity.

Example 5

Transformation in Tobacco

The leaf disc method was used for tobacco transformation (Savda and Binns, 2000). Approximately 1 $cm^2$-size leaf discs were cut from the upper 2-3 leaves of 3-4 weeks old tobacco plants grown in jam bottles on MS medium under aseptic conditions and used as explants for *Agrobacterium*-mediated transformation. These leaf discs were co-cultivated in the *Agrobacterium* bacterial suspension containing the promoter construct(s) at an $OD_{600}$ of ~0.6 in liquid MS medium for 20 minutes. The leaf discs were subsequently blotted on sterile 3 MM Whatman sheet piece and placed on MS medium solidified on 0.8% agar containing 0.1 mg/l Naphthalene acetic acid (NM) and 1 mg/l BAP in diffused light for two and a half days at 28° C. The leaf discs were washed thoroughly with a bacteriostatic agent, cephotaxime at 500 mg/l and discs were placed on selection medium (0.8% agar solidified MS medium containing 0.1 mg/l NAA and 1 mg/l BAP, 500 mg/l cephotaxime and 50 mg/l kanamycin) in light for one to one and a half months. Putative transgenic shoot buds were excised and placed on 0.8% agar solidified MS medium containing 50 mg/l kanamycin for rooting. The rooted plants were excised and a section of stem having at least one node were further put on a second round of selection on rooting medium. Those plants which rooted again were then shifted to pots in greenhouse till maturity.

Example 6

Analysis of Transformants

Putative transgenic plants were checked for the presence of T-DNA region by performing PCR with gene or promoter-specific primers. Genomic DNA was then isolated using the protocol of Dellaporta et al., (1983). To detect the activity of the reporter gene in different tissues, hand-cut sections of leaf blade/root were stained overnight in X-Gluc (5-Bromo-4-chloro-3-indolyl β-D-glucuronide) solution at 37° C. and de-stained subsequently in 1:3 acetone:ethanol till chlorophyll was removed completely, and photographed under a compound microscope (FIG. 4). For GUS fluorometry analysis, ca. 100 mg leaf tissue was used as described by Jefferson (1987).

ADVANTAGES OF THIS INVENTION

1. Identification of a promoter which is active in both monocots and dicots
2. Identification of a strong promoter for constitutive expression in rice.
3. Identification of a promoter showing tissue-specific expression.
4. Identification of a promoter to drive expression of a gene when gene pyramiding is to be achieved to avoid gene silencing when the same promoter is driving two different genes.

REFERENCES CITED

References by

U.S. Patent Documents

| 6,528,701 | March, 2003 | Wang et al. | 800/278 |
| 6,713,665 | March, 2004 | Crane III et al. | 800/298 |
| 6,693,227 | February, 2004 | Gittins et al. | 800/287 |
| 6,664,387 | December, 2003 | Chung et al. | 536/24 |
| 5,824,857 | October, 1998 | Beachy et al. | 800/287 |

OTHER REFERENCES

1. An, G., Ebert, P. R., Mitra, A. and Ha, S. B. (1988). Binary Vectors. Plant Mol Biol Manual A3: 1-19.
2. Bhattacharyya-Pakrasi, M., Peng, J., Elmer, J. S., Laco, G., Shen, P., Kaniewska, M. B., Kononowizc, H., Wen, F., Hodges, T. K. and Beachy, R. N. (1993). Specificity of a promoter from the rice tungro bacilliform virus for expression in phloem tissues. Plant J. 4(1): 71-79.
3. Chu, C.-C. (1978). The N6 medium and its applications to anther culture of cereal crops. In: Proceedings of Symposium on Plant Tissue Culture. Science Press, pp 43-50.
4. Cornejo, M. J., Luth, D., Blankenship, K. M., Anderson, O. D. and Blechl, A. E. (1993). Activity of a maize ubiquitin promoter in transgenic rice. Plant Mol. Biol. 23: 567-581.
5. Dellaporta, S. L., Wood, J. and Hicks, J. B. (1983). A plant DNA minipreparation, Ver. II. Plant Mol. Biol. Rep1 19-21.
6. Gamborg, O. L., Miller, R. A., and Ojima, K. (1968). Nutrient requirements of suspension cultures of soybean root cells. Exp Cell Res 50, 151-158.
7. Goto, F., Yoshihara, T., Shigemoto, N., Toki, S, and Takaiwa, F. (1999). Iron fortification of rice seeds by the soybean ferritin gene. Nat. Biotechnol. 17: 282-286.
8. Jang, I. C., Choi, W. B., Lee, K. H., Song, S. I., Nahm, B. H. and Kim, J. K. (2002). High-level and ubiquitous expression of the rice cytochrome c gene OsCc1 and its promoter activity in transgenic plants provides a useful promoter for transgenesis of monocots. Plant Physiol. 129: 1473-1481.
9. Jefferson, R. A. (1987). Assaying chimeric genes in plants: The GUS gene fusion system. Plant Mol. Biol. Rep. 5: 387-405.
10. Jones, M. C., Gough, K., Dasgupta, I., Subba Rao, B. L., Cliffe, J., Qu, R., Shen, P., Kaniewska, M., Blakebrough, M., Davies, J. W., Beachy, R. N. and Hull, R. (1991). Rice tungro disease is caused by an RNA and a DNA virus. J Gen Virol 72: 757-761.
11. Klöti, A., Henrich, C., Bieri, S., He, X., Chen, G., Burkhardt, P. K., Wünn, J., Lucca, P., Hohn, T., Potrykus, I. and Fotterer, J. (1999). Upstream and downstream sequence elements determine the specificity of the rice tungro bacilliform virus promoter and influence RNA production after transcription initiation. Plant Mol. Biol. 40: 249-266.
12. Kyozuka, J., Fujmoto, H., Izawa, T. and Shimamato, K. (1991). Anaerobic induction and tissue-specific expression of maize Adh1 promoter in transgenic rice plants and their progeny. Mol. Gen. Genet. 228: 40-48.
13. Kyozuka, J., McElroy, D., Hayakawa, T., Xie Y., Wu, R. and Shimamato, K. (1993). Light-regulated and cell-specific expression of tomato rbcS-gusA and rice rbcS-gusA fusion gene in transgenic rice. Plant Physiol. 102: 991-1000.
14. Matsuoka, M., Kyozuka, J., Shimamoto, K. and Kano-Murakami, Y. (1994). The promoters of two carboxylases in a C4 plant (maize) direct cell-specific, light-regulated expression in a C3 plant (rice). Plant J. 6(3): 311-319.
15. McElroy, D., Blowers, A. D., Jenes, B. and Wu, R. (1991). Construction of expression vectors based on the rice actin1 (Act1) 5' region for use in monocot transformation. Mol. Gen. Genet. 231: 150-160.
16. Murashige, T. and Scoog, F. (1962). A revised medium for rapid growth and bio assays with tobacco tissue culture. Planta 157, 385-391.
17. Nath, N., Mathur, S, and Dasgupta, I. (2002). Molecular analysis of two complete rice tungro bacilliform virus sequences from India. *Arch. Virol.* 147: 1173-1187.
18. Savda, M. and Binns, A. N. (2000). Introduction of DNA into Plants in Gene Transfer Methods pg. 159-192, edited by Norton, P. A. and Steel, L. F. Eaton publishing, Natick, Mass., USA.
19. Terada, R. and Shimamoto, K. (1990). Expression of CaMV 35S-GUS gene in transgenic rice plants. Mol. Gen. Genet. 220: 389-392.

20. Toki, S., Takamatsu, S., Nojiri, C., Ooba, S., Anzai, H., Iwata, M., Christensen, A. H., Quail, P. H. and Uchimiya, H. (1992). Expression of a maize ubiquitin gene promoter-bar chimeric gene in transgenic rice plants. Plant Physiol. 100: 1503-1507.
21. Wang, M. B., Upadhyaya, N. M., Brettell, R. I. S, and Waterhouse, P. M. (1997). Intron-mediated improvement of a selectable marker gene for plant transformation using *Agrobacterium tumefaciens*. J. Genet. Breed. 51: 325-334.
22. Wilmink, A., van de Ven, B. C. and Dons, J. J. (1995). Activity of constitutive promoters in various species from the *Liliaceae*. Plant Mol. Biol. 28: 949-955.
23. Xu, D., McElroy, D., Thornburg, R. W. and Wu, R. (1993). Systemic induction of a potato pin2 promoter by wounding, methyl jasmonate, and abscisic acid in transgenic rice plants. Plant Mol. Biol. 22: 573-588.
24. Ye, X., Al-Babili, S., Kloti, A., Zhang, J., Lucca, P., Beyer, P. and Potrykus, I. (2000). Engineering the provitamin A (beta-carotene) biosynthetic pathway into (carotenoid-free) rice endosperm. Science 287: 303-305.21.
25. Yin, Y. and Beachy, R. N. (1995). The regulatory regions of the rice tungro bacilliform virus promoter and interacting nuclear factors in rice (*Oryza sativa* L.). Plant J. 7(6): 969-980.
26. Yin, Y., Chen, L. and Beachy, R. N. (1997). Promoter elements required for phloem-specific gene expression from the RTBV promoter in rice. Plant J. 12(5): 1179-1188.

TABLE 1

| SEQUENCE NAME | SEQ ID NO | LENGTH (bp) |
| --- | --- | --- |
| Fl | SEQ ID NO: 1 | 876 |
| UD1 | SEQ ID NO: 2 | 818 |
| UD2 | SEQ ID NO: 3 | 789 |
| UD3 | SEQ ID NO: 4 | 754 |
| UD4 | SEQ ID NO: 5 | 718 |
| UD5 | SEQ ID NO: 6 | 681 |
| UD6 | SEQ ID NO: 7 | 671 |
| DD1 | SEQ ID NO: 8 | 862 |
| DD2 | SEQ ID NO: 9 | 793 |
| DD3 | SEQ ID NO: 10 | 691 |
| DD4 | SEQ ID NO: 11 | 581 |
| DD5 | SEQ ID NO: 12 | 426 |
| DD6 | SEQ ID NO: 13 | 325 |
| DD7 | SEQ ID NO: 14 | 289 |

TABLE 1-continued

| SEQUENCE NAME | SEQ ID NO | LENGTH (bp) |
| --- | --- | --- |
| DD8 | SEQ ID NO: 15 | 254 |
| FP1 | SEQ ID NO: 16 | 28 |
| FP2 | SEQ ID NO: 17 | 32 |
| FP3 | SEQ ID NO: 18 | 33 |
| FP4 | SEQ ID NO: 19 | 35 |
| FP5 | SEQ ID NO: 20 | 36 |
| FP6 | SEQ ID NO: 21 | 34 |
| FP7 | SEQ ID NO: 22 | 34 |
| RP1 | SEQ ID NO: 23 | 35 |
| RP2 | SEQ ID NO: 24 | 33 |
| RP3 | SEQ ID NO: 25 | 30 |
| RP4 | SEQ ID NO: 26 | 30 |
| RP5 | SEQ ID NO: 27 | 27 |
| RP6 | SEQ ID NO: 28 | 28 |
| RP7 | SEQ ID NO: 29 | 31 |
| RP8 | SEQ ID NO: 30 | 31 |
| RP9 | SEQ ID NO: 31 | 28 |

TABLE 2

Expression patterns observed in vegetative tissues for RTBV promoter construct in rice and tobacco transgenics

| CONSTRUCT | EXPRESSION PATTERN | |
| --- | --- | --- |
| | RICE | TOBACCO |
| FL | FL TYPE | FL TYPE |
| UD1 | FL TYPE | FL TYPE |
| UD2 | FL TYPE | FL TYPE |
| UD3 | FL TYPE | FL TYPE |
| UD4 | FL TYPE | FL TYPE |
| UD5 | FL TYPE | NO EXPRESSION |
| DD3 | FL TYPE | — |
| DD4 | FL TYPE | — |
| DD5 | NO EXPRESSION | FL TYPE |
| DD6 | NO EXPRESSION | FL TYPE |
| DD7 | CONSTITUTIVE | FL TYPE+ |
| DD8 | CONSTITUTIVE | FL TYPE+ |

FL TYPE IN RICE: Constitutive expression in young age and vascular-specific in mature age
FL TYPE IN TOBACCO: Vascular specific expression only
FL TYPE+ IN TOBACCO: Only cotyledonary leaves show constitutive expression but rest of the vegetative tissues show vascular specific expression
—: Indicates plants not transformed with the specific construct

The invention claimed is:

1. An isolated promoter from Rice Tungro Bacilliform Virus (RTBV promoter) consisting of a fragment of SEQ ID NO: 1, wherein the fragment has the RTBV promoter activity of SEQ ID NO: 1.

2. The isolated promoter according to claim 1, wherein said promoter comprises at least bases 1-254 of SEQ ID NO: 1.

3. The isolated promoter according to claim 1, wherein said promoter is selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14 and SEQ ID NO: 15.

4. A chimeric plasmid DNA construct, wherein the promoter according to claim 1 is operably linked to a heterologous nucleic acid sequence.

5. A chimeric plasmid DNA construct, wherein the promoter according to claim 3 is operably linked to a heterologous nucleic acid sequence.

6. The chimeric plasmid DNA construct according to claim 4, wherein said heterologous nucleic acid sequence encodes a polypeptide capable of conferring improved agronomic traits to a plant.

7. The chimeric plasmid DNA construct according to claim 5, wherein said heterologous nucleic acid sequence encodes a polypeptide capable of conferring improved agronomic traits to a plant.

8. The chimeric plasmid DNA construct according to claim 4, wherein said plasmid is a plant transformation vector.

9. The chimeric plasmid DNA construct according to claim 5, wherein said plasmid is a plant transformation vector.

10. A recombinant cell harboring the chimeric plasmid DNA construct according to claim 4.

11. A recombinant cell harboring the chimeric plasmid DNA construct according to claim 5.

12. The recombinant cell according to claim 10, wherein the said cell is selected from E. coli or Agrobacterium.

13. The recombinant cell according to claim 11, wherein the said cell is selected from E. coil or Agrobacterium.

14. A transformed plant or cells harboring a heterologous nucleic acid sequence operably linked to the promoter as claimed in claim 1.

15. A transformed plant or cell harboring a heterologous nucleic acid sequence operably linked to the promoter as claimed in claim 3.

16. A progeny derived from a transgenic plant according to claim 14, wherein a progeny contains a heterologous nucleotide sequence operably linked to the promoter.

17. A seed derived from a transgenic plant according to claim 14, wherein a seed contains a heterologous nucleotide sequence operably linked to the promoter.

18. The transgenic plant according to claim 14, wherein said plant is a monocot or a dicot.

19. The transgenic plant according to claim 18, wherein said monocot species is selected from the group consisting of rice, maize, wheat, barley and sorghum.

20. The transgenic plant according to claim 18, wherein said dicot species is selected from the group consisting of tobacco, tomato, pea, soybean, brassicas, chickpea, cotton and pigeon pea.

21. A method for expression of a heterologous nucleic acid operably linked to RTBV promoter in a plant, wherein the said method comprises the steps of:

a) constructing the chimeric plasmid DNA construct according to claim 9, b) mobilizing the construct of step (a) into *Agrobacterium* strain to produce recombinant *Agrobacterium* strains, c) obtaining suitable explants from a plant for plant transformation, d) co-culturing the explants, of step (c) with the recombinant *Agrobacterium* strain of step (b) to produce transformed plant cells, e) selecting transformed plant cells of step (d), f) obtaining shoots from transformed plant cells of step (e), g) obtaining rooted plantlets from the shoots of step (f), h) growing the rooted plantlets of step (g) to produce transformed plants.

22. The method of expression according to claim 21, wherein said RTBV promoter is selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14 and SEQ ID NO: 15.

* * * * *